United States Patent
Youn et al.

(10) Patent No.: US 7,192,743 B2
(45) Date of Patent: Mar. 20, 2007

(54) METHOD OF PRODUCING TEICOPLANIN

(75) Inventors: Deok-Joong Youn, Chungcheongbuk-Do (KR); Ho-Myeung Ryu, Chungcheongnam-Do (KR); Kang-Hee Lee, Chungcheongbuk-Do (KR); Dae-Sung Lim, Chungcheongbuk-Do (KR); In-Kyu Lee, Seoul (KR); Sung-Woo Kim, Seoul (KR); Hyun-Ki Paeng, Chungcheongbuk-Do (KR); Kyung-Hoi Cha, Gyeonggi-Do (KR)

(73) Assignee: Dong Kook Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 11/106,717

(22) Filed: Apr. 15, 2005

(65) Prior Publication Data

US 2005/0245481 A1    Nov. 3, 2005

(30) Foreign Application Priority Data

Apr. 16, 2004  (KR) ............... 10-2004-0026354

(51) Int. Cl.
*C12P 1/00* (2006.01)
*C12P 21/04* (2006.01)

(52) U.S. Cl. ............... 435/71.3; 435/41
(58) Field of Classification Search ............ 435/41, 435/71.3
See application file for complete search history.

(56) References Cited

U.S. PATENT DOCUMENTS

| 4,239,751 A | 12/1980 | Coronelli et al. | |
| 4,994,555 A * | 2/1991 | Panzone et al. | ............ 530/344 |

FOREIGN PATENT DOCUMENTS

| EP | 0 241 758 A2 | 10/1987 |
| EP | 0 479 086 A2 | 4/1992 |
| KR | 2000-0066479 A | 11/2000 |
| KR | 2003-0017067 A | 3/2003 |
| KR | 2003-0034949 A | 5/2003 |
| KR | 2003-0092504 A | 12/2003 |
| KR | 10-2004-0008745 A | 1/2004 |

OTHER PUBLICATIONS

ASTEC, "Experimental protocols for preparative purification using Macrocyclic Glycopeptide chiral stationary phases", Advanced Separation Technologies Inc., 2003, (at the web: www.astecusa. com), pp. 1-10.*
Bardone, M.R., et al., "Teichomycins, New Antibiotics from *Actinoplanes Teichomyceticus* Nov. Sp. II. Extraction and Chemical Characterization," *J. Antibiotics 31*:170-177, Japan Antibiotics Research Association (1978).
Heydorn, A., et al., "Biosynthetic Studies of the Glycopeptide Teicoplanin by $^1$H and $^{13}$C NMR," *J. Biol. Chem. 275*:6201-6206, American Society for Biochemistry and Molecular Biology, Inc. (2000).
Lee, J.C., et al., "Improved production of teicoplanin using adsorbent resin in fermentations," *Lett. Appl. Microbiol. 37*:196-200, Blackwell Scientific Publications (Sep. 2003).
Riva, E., et al., "Column Purification and HPLC Determination of Teicoplanin and A40926," *Chromatographia 24*:295-301, Friedr. Viewag & Verlagsgesellschaft mbH (1987).
Korean Patent Abstracts, Korean Intellectual Property Office, English language abstract for KR 2000-0066479 A, cited on Form PTO/SB/08A as document FP2.
Dialog File 351, Accession No. 15632244, Derwent WPI English language abstract for KR 2003-0017067 A, cited on Form PTO/SB/08A as document FP3.
Dialog File 351, Accession No. 15947190, Derwent WPI English language abstract for KR 2003-0034949 A, cited on Form PTO/SB/08A as document FP4.
Dialog File 351, Accession No. 16106872, Derwent WPI English language abstract for KR 2003-0092504 A, cited on Form PTO/SB/08A as document FP5.
Dialog File 351, Accession No. 16066911, Derwent WPI English language abstract for KR 10-2004-0008745 A, cited on Form PTO/SB/08A as document FP6.

* cited by examiner

*Primary Examiner*—Sandra E. Saucier
*Assistant Examiner*—Satyendra K. Singh
(74) *Attorney, Agent, or Firm*—Sterne, Kessler, Goldstein & Fox PLLC

(57) ABSTRACT

Disclosed is a method of producing teicoplanin. The method includes purifying teicoplanin from a culture broth, obtained by culturing microorganisms capable of producing teicoplanin by a porous adsorption resin under selective elution conditions and recovering highly pure teicoplanin using activated carbon and/or ultrafiltration. In this regard, the method can further include ultrafiltration as pre-treatment before the culture broth is adsorbed into the porous adsorption resin so as to increase the purity of teicoplanin.

4 Claims, 1 Drawing Sheet

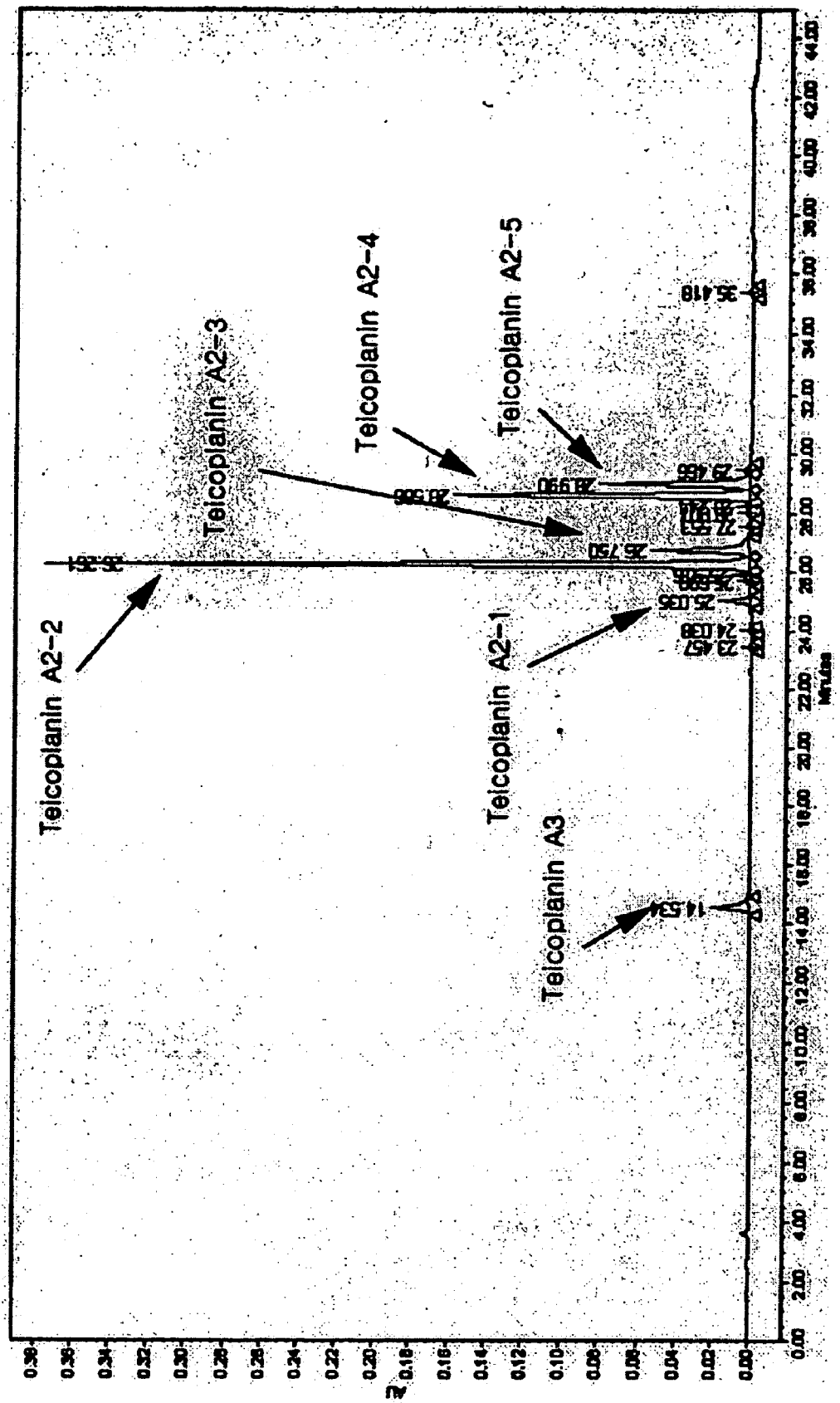

METHOD OF PRODUCING TEICOPLANIN

CROSS-REFERENCE TO RELATED APPLICATIONS

This application claims priority to Korean Patent Appl. No. 10-2004-0026354, filed Apr. 16, 2004, which is incorporated by reference herein in its entirety.

BACKGROUND OF THE INVENTION

1. Field of the Invention

The present invention pertains to a method of cultivating a microorganism, which is capable of producing teicoplanin, and of producing teicoplanin using a culture broth. The present invention provides a method of economically producing highly pure teicoplanin, in which teicoplanin is produced at a stable, neutral pH range.

2. Description of the Prior Art

Recently, it is regarded as a serious problem that antibiotic-resistant microorganisms are spreading due to abuse of antibiotics. With respect to this, teicoplanin, which is a glycopeptide antibiotic, is considered a last defense line to infectious diseases. Teicoplanin acts against gram-positive bacteria, such as methicillin-resistant Staphylococcus aureus (MRSA), coagulase-negative Staphylococcus, Clostridium and Enterococcus. Teicoplanin is a complex of five kinds of A2 components, having different fatty acid branched chains, and A3, having an aglycone structure in which a sugar moiety of N-acyl-β-D-glucosamine, including the fatty acid branched chain, is removed from a basic structure of A2. As used herein, teicoplanin is designated by the teicoplanin A2 complex acting as an effective component.

Generally, a chemical synthetic process or a bio-synthetic process using a culture of microorganism is adopted to produce antibiotics in commercial quantities. The glycopeptide antibiotics have a complicated chemical structure, in which sugar is bonded to a peptide skeleton. Hence, teicoplanin and the glycopeptide antibiotics commercialized as pharmaceuticals are produced according to the bio-synthetic process, which is a so-called fermentation process. In the bio-synthetic process, various impurities, such as medium components and metabolic products, are produced concomitantly with the antibiotic. Accordingly, a number of separation and purification processes are required to purify the antibiotics, which are critical factors in economically producing a highly pure antibiotic.

Teicoplanin, a glycopeptide antibiotic produced from *Actinoplanes teichomyceticus*, was first reported in *J. Antibiotics* 31:170–177 (1978). Efforts have been made to separate teicoplanin from a culture broth of microorganism and purify teicoplanin using various processes so as to produce pharmaceutical grade teicoplanin. According to the above journal and U.S. Pat. No. 4,239,751, a culture broth is divided into a mycelial cake and a filtrate. The mycelial cake is extracted with acetone and the extract is extracted again with butanol at acidic pH. The filtrate, made free from the mycelial mass by filtration, is extracted with butanol at acidic pH. Subsequently, the butanol layers are concentrated by vacuum distillation to form precipitates. The precipitates are mixed with each other, and the mixture is purified with Sephadex LH20 column. The eluate from Sephadex LH20 is further purified with an acidic ion exchange resin, such as IR-120 and Dowex 50, and then, the teicoplanin is precipitated at 4° C. However, the process in U.S. Pat. No. 4,239,751 has disadvantages in that the purification method is very complicated. Furthermore, Sephadex LH 20 is too expensive to apply in a large scale production. Another disadvantage is that the recovery and purity of teicoplanin are poor.

Korean Pat. No. 36780 recites a process of directly extracting teicoplanin from a culture broth, in which a water-miscible organic solvent, such as acetone, n-propanol, and acetonitrile, is added without separating mycelia. Furthermore, Korean Pat. No. 118034 discloses a process of producing teicoplanin by directly adding a strongly acidic cation exchange resin, such as Dow XFS-43278.00 and Diaion SK-102, to a culture broth. However, the processes in Korean Pat. Nos. 367890 and 118034 are disadvantageous in that even though a process of directly extracting teicoplanin from the culture broth is more simplified than in the case of U.S. Pat. No. 4,239,751, it is difficult to employ in a production process because a great amount of organic solvent is inevitably used to extract teicoplanin, which may cause environmental pollution. In addition, it is difficult to produce highly pure teicoplanin by only modifying the extraction process.

Many studies have been carried out to purify teicoplanin by column chromatography using synthetic resins, as suggested by Heydorn et al., *J. Biochem.* 275:6201–6206 (2000), and as disclosed in European Pat. No. 241,758, Korean Pat. No. 321304, Korean Pat. Laid-Open Publication No. 2003-0017067, and Korean Pat. Laid-Open Publication No. 2003-0034949. Additionally, European Pat. No. 241,758 discloses a process of purifying teicoplanin using a polyamide resin. Further, Korean Pat. No. 184644 discloses an extraction process of teicoplanin from mycelium at alkaline pH, thereby simplifying the complicated extraction process of U.S. Pat. No. 4,239,751. In Korean Pat. No. 184644, after extraction of teicoplanin, the basic culture broth is neutralized, and then purified using the polyamide resin according to a procedure of European Pat. 241,758. However, when the purified teicoplanin was analyzed by HPLC (high performance liquid chromatography), the purity of teicoplanin was not more than 85% and decolorization was poor. Therefore, a further purifying process is required so as to produce highly pure teicoplanin. In order to study a biosynthetic pathway of teicoplanin, Heydorn et al. had separated and purified teicoplanin according to a chromatography process using an ion-exchange resin (Amberlite IRA958) and a hydrophobic adsorption resin (Diaion HP2MGL). However, the method suggested by Heydorn et al. is disadvantageous in that it is inconvenient because acetic acid has to be continuously added to the basic solution passing through the resin to neutralize it and prevent an epimerization. Additionally, when the purity of teicoplanin is analyzed by HPLC after the purified solution is desalted, concentrated, and lyophilized to produce teicoplanin powder, the purity is only about 50% to 60% (w/w). Accordingly, it is undesirable to use the teicoplanin powder as a pharmaceutical ingredient.

Meanwhile, porous adsorption resins have been frequently used to purify glycopeptide antibiotics, including teicoplanin. In detail, Korean Pat. No. 321304 discloses a process of purifying teicoplanin, which includes a hydrophobic interaction chromatography step using a neutral adsorption resin and a lectin-immobilized affinity chromatography step. At this time, the neutral adsorption resin includes XAD 16, HP 20, silica gel, and activated carbon. In this patent, a filtered culture broth is directly purified by the hydrophobic adsorption chromatography using HP-20 and the like, and thus, it is convenient to conduct the process. However, in case that the filtered culture broth extracted from a basic solution is adsorbed into a resin, such as HP 20, according to the process of Korean Pat. No. 321304, a great amount of teicoplanin is lost in an adsorption step, and the purity of teicoplanin eluted by a methanol concentration gradient is very low. Moreover, it is necessary to remove methanol in order to apply the solution to a lectin-immobilized resin. Furthermore, it is not desirable to apply the solution to a lectin-immobilized resin in the large scale production because of the cost of lectin-immobilized resins.

According to Korean Pat. Laid-Open Publication No. 2003–0017067, after teicoplanin of a culture broth is adsorbed into a porous adsorption resin, the porous adsorption resin is washed with diluted hydrochloric acid, and teicoplanin is desorbed from the adsorption resin using a mixed solution of water and acetone. The eluting solution containing teicoplanin is concentrated by vacuum distillation, treated with an activated carbon, and subjected to a precipitation process, and thereby teicoplanin is purified. However, the process in Korean Pat. Laid-Open Publication No. 2003-0017067 is disadvantageous in that the stability and activity of teicoplanin are decreased because the pH of the liquid that is processed is continuously changed to acid or basic. Other disadvantages are that the life-time and exchange cycle of the resin are shortened, and recovery yield and purity of teicoplanin are poor because of moieties irreversibly adsorbed into the resin. Meanwhile, Korean Pat. Laid-Open Publication No. 2003-0034949 discloses a method of producing teicoplanin, which includes roughly purifying teicoplanin from a culture broth through a two-stage process using porous adsorption resins, and precipitating teicoplanin at low temperatures and slightly acidic pH. However, this method has disadvantages in that the use of a large amount of organic solvent, such as n-propanol, isopropanol, and methanol, contributes to pollution, and that precipitation at low temperature and slightly acidic pH reduces the solubility and activity of teicoplanin.

Furthermore, it is difficult to purify teicoplanin of 95% or higher purity through only a purifying process using porous adsorption resins. Accordingly, many studies have been carried out with reverse phase resins to separate and purify teicoplanin from the culture broth. For example, references can be made to a process suggested by Riva et al., *Chromatographia* 24:295–301 (1987), Korean Pat. No. 40453, and Korean Pat. Laid-Open Publication Nos. 2003-0092504 and 10-2004-0008745. Riva et al. proposed a process of purifying teicoplanin using a Lichrosorb RP-18 column. Korean Pat. No. 40453 discloses a process of separating each single component of teicoplanin A2 complex using a silanized silica gel column. At this time, in the case of using the reverse phase resin, it is possible to produce more pure teicoplanin than in the case of a separation process using a combination of an extraction, an ion-exchange resin, and a porous adsorption resin. However, Korean Pat. No. 40453 is problematic in economic efficiency because the reverse phase resin and high pressure chromatography system are both costly. Further, acetonitrile, which is toxic to the human nervous system, is used in eluting teicoplanin from the reverse phase resin in Korean Pat. No. 40453. Furthermore, Korean Pat. Laid-Open Publication No. 2003-0092504 proposes a method of purifying teicoplanin, in which a mycelium-free culture broth directly passes through a reverse phase resin, such as YMC-gel ODS-A, or in which a roughly purified liquid, pre-treated with a cation-exchange resin, an anion-exchange resin, or a adsorption resin, passes through YMC-gel ODS-A. However, this method is disadvantageous in that acetonitrile is used for the elution, and thus, it is difficult to control the residual amounts of acetonitrile. Another disadvantage is that production costs are inevitably increased because the reverse phase resin must frequently be replaced with a new one. Korean Pat. Laid-Open Publication No. 10-2004-0008745 recites a process of purifying teicoplanin from a culture broth of a microorganism capable of producing teicoplanin, which includes a primary purifying step using a synthetic adsorbent, a secondary purifying step using a cation-exchange resin, a catalytic resin, or a chelate resin, a tertiary purifying step using a reverse phase resin, and a final lyophilization step. However, the process in Korean Pat. Laid-Open Publication No. 10-2004-0008745 is disadvantageous in that even though highly pure teicoplanin is produced, the process is very complicated because the process includes a number of steps, and recovery yield of teicoplanin is very low. Moreover, the process in Korean Pat. Laid-Open Publication No. 10-2004-0008745 has the same disadvantages, regarding the use of the reverse phase resin, as the process in Korean Pat. Laid-Open Publication No.2003-0092504.

Accordingly, conventional technologies of purifying teicoplanin from the culture broth are problematic in that highly purified teicoplanin is not readily produced, stability of teicoplanin is not maintained, the organic solvents toxic to humans are used during the purification, recovery yield is relatively low, and production costs are relatively high. Hence, there remains a need to develop an improved process of purifying teicoplanin.

SUMMARY OF THE INVENTION

The present invention has been made keeping in mind the above disadvantages, and to provide inexpensive and safe methods for producing highly pure teicoplanin.

The present invention is directed to a method of producing teicoplanin, comprising: (a) eluting a culture broth of *Actinoplanes teichomyceticus* strain, capable of producing teicoplanin, from a porous adsorption resin to produce a liquid containing teicoplanin; and (b) treating the liquid containing teicoplanin with an activated carbon to recover teicoplanin. The method can further comprise ultrafiltering the teicoplanin of (b).

The invention is also directed to a method of producing teicoplanin, comprising: (a) eluting a culture broth of *Actinoplanes teichomyceticus* strain, capable of producing teicoplanin, from a porous adsorption resin to produce a liquid containing teicoplanin; and (b) ultrafiltering the liquid containing teicoplanin to recover teicoplanin as an ultrafiltration permeate. The method can further comprise treating the ultrafiltration permeate with an activated carbon.

The invention is also directed to a method of producing teicoplanin, comprising: (a) ultrafiltering a culture broth of *Actinoplanes teichomyceticus* strain, capable of producing teicoplanin, to produce an ultrafiltration permeate; (b) eluting the ultrafiltration permeate from a porous adsorption resin to produce a liquid containing teicoplanin; and (c) treating the liquid containing teicoplanin with an activated carbon to recover teicoplanin. The method can further comprise ultrafiltering the teicoplanin of (c).

The invention is also directed to a method of producing teicoplanin, comprising: (a) ultrafiltering a culture broth of *Actinoplanes teichomyceticus* strain, capable of producing teicoplanin, to produce an ultrafiltration permeate; (b) eluting the ultrafiltration permeate from a porous adsorption resin to produce a liquid containing teicoplanin; and (c) ultrafiltering the liquid to recover teicoplanin. The method can further comprise treating the teicoplanin of (c) with an activated carbon.

In some embodiments, the *Actinoplanes teichomyceticus* strain is *Actinoplanes teichomyceticus* DKB 53.

In some embodiments, the eluting of teicoplanin from the porous adsorption resin is performed using an elution agent comprising 40% to 90% (v/v) of one or more of C1 to C4 water-miscible alcohols with a pH of 6.0 to 8.0.

In some embodiments, the eluting of teicoplanin from the porous adsorption resin is performed using an elution agent comprising 40% to 90% (v/v) of one or more of C3 to C6 water-miscible ketones with a pH of 6.0 to 8.0.

In some embodiments, the eluting of teicoplanin from the porous adsorption resin is performed using an elution agent comprising a neutral salt. In some embodiments, the neutral salt can be 0.05 to 0.5 M of sodium salt or potassium salt.

In some embodiments, the porous adsorption resin has a pore radius of 20 Å to 300 Å, and is selected from the group consisting of DOWEX OPTIPORE L493, DOWEX OPTIPORE L323, DOWEX OPTIPORE SD-2, DIAION HP20, DIAION HP2MG, DIAION HP20SS, SEPABEADS SP825, SEPABEADS SP 850, SEPABEADS SP 700, SEPABEADS SP207, SEPABEADS SP20SS, AMBERLITE XAD4, AMBERLITE XAD7, AMBERLITE XAD16, AMBERLITE XAD1600T, and combinations thereof.

In some embodiments, the activated carbon is added into the liquid containing teicoplanin by 0.2 to 5 times more weight than teicoplanin to adsorb the liquid containing teicoplanin at 10° C. to 40° C. within 12 hours. In some embodiments, the activated carbon is added into the liquid containing teicoplanin by 0.5 to 3 times more weight than teicoplanin to adsorb the liquid containing teicoplanin at 18° C. to 36° C. within 0.5 to 3 hours.

In some embodiments, the treating of the liquid containing teicoplanin using the activated carbon comprises directly adding the activated carbon into a liquid with a pH of 6 to 8, passing through the porous adsorption resin, or adding the activated carbon into the liquid, which is diluted with water.

The activated carbon can be selected from the group consisting of AQUA NUCHAR, NUCHAR SA, NUCHAR SA-20, NUCHAR SA-30, NUCHAR SN, NUCHAR SN-20, NORIT A SUPRA EUR, NORIT B SUPRA EUR, NORIT C EXTRA USP, NORIT CN 1, NORIT CN 3, DARCO G 60, DARCO KB, DARCO KB-B, NORIT E SUPRA USA, NORIT GBG, NORIT PN2, NORIT ROX 0.8, NORIT SX 1, NORIT SX 1G, NORIT SX 2, NORIT SX PLUS, NORIT SX SUPRA E 153, NORIT SX ULTRA, CAL 12X40, GW 12X40, and combinations thereof.

In some embodiments, the treating of the liquid containing teicoplanin using the activated carbon comprises filtering the liquid containing teicoplanin to remove the activated carbon from the liquid containing teicoplanin, adsorbing the filtered liquid into the porous adsorption resin, washing the porous adsorption resin using water, and eluting teicoplanin using 40% to 90% (v/v) of one or more C1 to C4 water-miscible organic solvents.

In some embodiments, the porous adsorption resin can have a pore radius of 20 Å to 300 Å, and can be selected from the group consisting of DOWEX OPTIPORE L493, DOWEX OPTIPORE L323, DOWEX OPTIPORE SD-2, DIAION HP20, DIAION HP2MG, DIAION HP20SS, SEPABEADS SP825, SEPABEADS SP 850, SEPABEADS SP 700, SEPABEADS SP207, SEPABEADS SP20SS, AMBERLITE XAD4, AMBERLITE XAD7, AMBERLITE XAD16, AMBERLITE XAD1600T, and combinations thereof.

In some embodiments, an ultrafiltration membrane, used when the culture broth or liquid containing teicoplanin is ultrafiltered, has a molecular weight cut-off of 3000 Da to 100000 Da.

In some embodiments, the ultrafiltration is carried out at a temperature of 8° C. to 30° C., an input pressure of 0 to 4 bar, and a retentate pressure of 0 to 3.5 bar. In some embodiments, the ultrafiltration is carried out at a temperature of 12° C. to 18° C., an input pressure of 0 to 4 bar, and a retentate pressure of 0 to 3.5 bar.

In some embodiments, the ultrafiltration membrane can be made of polyether sulfone or regenerated cellulose, and can be selected from the group consisting of Biomax, Ultracel, PT and PL of Prostak module, Helicon, Sartocon, Ultrasart, OMEGA, ALPHA, REGEN, SUPOR, Filmtec, and Kvick.

BRIEF DESCRIPTION OF THE DRAWINGS

FIG. 1 illustrates results regarding an HPLC analysis of teicoplanin.

DETAILED DESCRIPTION OF THE INVENTION

In the present invention, any strain of microorganism can be used to produce highly pure teicoplanin as long as the strain is capable of producing teicoplanin. An example of microorganism capable of producing teicoplanin includes *Actinoplanes teichomyceticus*, such as *Actinoplanes teichomyceticus* DKB53 (having deposit no. KCTC 10587BP, deposited Jan. 30, 2004 at Korea Research Institute of Bioscience and Biotechnology (KRIBB), #52, Oun-dong, Yusong-ku, Taejon 305-333, Republic of Korea, under the terms of the Budapest Treaty) and *Actinoplanes teichomyceticus* ATCC31121 (U.S. Pat. No. 4,239,751). In some embodiments, *Actinoplanes teichomyceticus* DKB53 (KCTC 10587BP) is used to produce teicoplanin. Additionally, the microorganism can be optimally cultured under the following conditions.

A carbon source used in a culture medium for fermentation includes, but is not limited to, glucose, maltose, sucrose, and galactose. In consideration of the costs of raw materials, starch can be used in the medium for seed culture and maltose can be used in a culture medium for culture production.

In the case of using maltose as a carbon source, the culture medium for teicoplanin production can include, e.g., 40 to 100 g/L of maltose, 3 to 5 g/L of yeast extract, 5 to 10 g/L of soybean flour, 5 to 10 g/L of cottonseed meal, 3 to 5 ml/L of corn steep liquor (CSL), 0.1 to 5 g/L of sodium chloride, and 0.1 to 10 mg/L of trace metal elements.

When *Actinoplanes teichomyceticus* DKB53 is cultivated, the range of optimum pH is about 6.8±0.2. The culture temperature can be from about 28° C. to 34° C.

Optimum culture conditions of *Actinoplanes teichomyceticus* DKB53 used to produce teicoplanin with high yield can include the following.

In an early step of the fermentation, the culture can be carried out at an air flow rate of about 1.0 to 1.5 vvm, pressure in a fermentation device can be maintained to 0.2 to 0.3 bar, the fermentation temperature can be 28° C. to 34° C., and the agitation can be carried out at an agitation speed of 140 to 200 rpm.

In a middle step of the fermentation, the agitation speed can be gradually increased to a speed range of 200 to 400 rpm within 48 to 90 hours from the start of fermentation. The reason for this is that a gradual increase of the agitation speed is useful in view of an oxygen utilization rate (OUR). In some embodiments, after the agitation speed is gradually increased, the air flow rate can be controlled to 0.4 to 0.8 vvm while the pressure in the fermentation device can be maintained to 0.1 to 0.2 bar, leading to proper control of partial oxygen pressure.

According to the present invention, a method of producing teicoplanin includes rough purification using a porous adsorption resin under a selective elution condition and recovering highly pure teicoplanin using an activated carbon or/and an ultrafiltration. In this regard, the method can further include ultrafiltration as pre-treatment before the culture broth is adsorbed into the porous adsorption resin to increase the purity of teicoplanin.

The term "culture broth" as used herein is denoted the filtered culture broth made substantially free from the mycelium.

After fermentation, the pH of the culture broth, in which the microorganism capable of yielding teicoplanin is cultured, and from which a mycelium is removed, is controlled to a neutral pH range of 6 to 8. In this respect, sodium hydroxide or hydrochloric acid can be used to control the pH of the culture broth to the neutral pH range. After the pH of the clarified or filterd culture broth is controlled as described above, it is not necessary to conduct a further pH control process. The pH of the clarified culture broth as a starting material in the purification step using the porous adsorption resin can be 6.5 to 7.5. At this time, it should be understood that the term "porous adsorption resin" as used herein is intended to include, but not limited to, a synthetic adsorbent with a pore radius of 20 Å to 300 Å, which is comprised of a polymer having (1) no ion-exchange groups, such as a polymer of styrene and divinyl benzene, (2) a cross-linked aromatic or aliphatic polymer, and (3) a methacryl adsorbent. In detail, examples of the porous adsorption resin include, but are not limited to, DOWEX OPTIPORE L493, DOWEX OPTIPORE L323, and DOWEX OPTIPORE SD-2, manufactured by Dow Chemical Co., DIAION HP20, DIAION HP2MG, DIAION HP20SS, SEPABEADS SP825, SEPABEADS SP850, SEPABEADS SP700, SEPABEADS SP207, and SEPABEADS SP20SS, manufactured by Mitsubishi Chemical Co., and AMBERLITE XAD4, AMBERLITE XAD7, AMBERLITE XAD16, and AMBERLITE XAD1600T, manufactured by Rohm & Haas Co.

After the porous adsorption resin is packed in a column, the culture broth is applied onto the column, or the porous adsorption resin is added into the culture broth in a vessel and a mixture is agitated to adsorb teicoplanin into the porous adsorption resin. In this regard, one or more of C1 to C4 water-miscible alcohols can be added to the neutral culture broth in an amount less than 40% (v/v), e.g., in an amount of 5% to 20% (v/v) to prevent adsorption of impurities into the porous adsorption resin and to prevent denaturing of teicoplanin due to an enzyme contained in the culture broth. The porous adsorption resin, including teicoplanin adsorbed thereinto, can be washed with a mixed liquid of 10% to 40% (v/v) of one or more of C1 to C4 alcohols or one or more of C3 to C6 ketones and water to sufficiently remove impurities or colored components therefrom.

Teicoplanin can be selectively eluted from the porous adsorption resin by controlling the salt concentration in the eluting agent. The eluting agent, used to elute teicoplanin adsorbed into the porous adsorption resin, can include (1) a neutral salt, e.g., 0.05 M to 0.5 M, (2) a mixed liquid of one or more of C1 to C4 alcohols or one or more of C3 to C6 ketones, and/or (3) water. The neutral salt can be, but is not limited to, a sodium salt, such as sodium chloride and sodium phosphate, and a potassium salt, such as potassium chloride. In some embodiments, the concentration of the salt added to the eluting agent is 0.1 to 0.3 M. In the case of using an eluting agent containing salt, teicoplanin is produced at a relatively high purity when compared to using a mixed liquid of water-miscible organic solvent or water, containing no salt, as the eluting agent. In addition, because the liquid added to the porous adsorption resin is maintained at neutral pH, an epimerization of teicoplanin, occurring when the liquid is basic, and the reduction of activity of teicoplanin, occurring when the liquid is acidic, are prevented.

Teicoplanin that has been purified by passing through the porous adsorption resin can be further purified by an activated carbon treating process, an ultrafiltration process, or a combined process of the activated carbon treating and ultrafiltration processes.

Activated carbon can be used to remove various impurities, such as colored components and substances with offensive odors, during the production of chemicals, foodstuffs and pharmaceuticals. Examples of commercial activated carbon useful in the present invention include, but are not limited to, AQUA NUCHAR, NUCHAR SA, NUCHAR SA-20, NUCHAR SA-30, NUCHAR SN, and NUCHAR SN-20, manufactured by MeadWestvaco Co., NORIT A SUPRA EUR, NORIT B SUPRA EUR, NORIT C EXTRA USP, NORIT CN 1, NORIT CN 3, DARCO G 60, DARCO KB, DARCO KB-B, NORIT E SUPRA USA, NORIT GBG, NORIT PN 2, NORIT ROX 0.8, NORIT SX 1, NORIT SX 1G, NORIT SX 2, NORIT SX PLUS, NORIT SX SUPRA E 153, and NORIT SX ULTRA, manufactured by NORIT Nederland B.V., and CAL 12X40 and GW 12X40, manufactured by Calgon Carbon Co. Additionally, activated carbon can be added directly to the liquid passing through the porous adsorption resin or added to it after dilution with water. In other words, the method of the present invention is advantageous in that the activated carbon can be directly added to liquid passing through the porous adsorption resin, or added to roughly purified liquid (once treated by porous adsorption resin) containing teicoplanin after a concentration of the water-miscible organic solvent or salt is reduced by addition of water, and thus, organic solvent removal, desalting, and concentration processes can be omitted.

After the teicoplanin content in the liquid passing through the porous adsorption resin is measured using HPLC (high performance liquid chromatography), e.g., according to a method as described in Japanese Pharmacopoeia, the activated carbon can be added to the liquid by a 0.2 to 5 times more amount than a measured teicoplanin. In some embodiments, the activated carbon is added to the liquid being processed by a 0.5 to 3 times more amount than the teicoplanin. After the activated carbon is added to the liquid, the pH of the liquid is measured to ensure that the pH is between about 6 to 8. The liquid is then agitated at 10° C. to 40° C. within 12 hours. In certain embodiments, the liquid is treated with the activated carbon at 18° C. to 36° C. for 0.5 to 3 hours, thereby preventing teicoplanin from being irreversibly adsorbed into the activated carbon and promoting the adsorption of the impurities, such as colored components, into the activated carbon.

After the liquid being processed is treated with activated carbon, the liquid can be filtered using a KS 80 filter (manufactured by Pall Co.) or Whatman filter paper 4 (manufactured by Whatman Int'l Ltd.) to remove the activated carbon from the liquid, and then is passed through the column, in which the porous adsorption resin is packed, or is adsorbed into the porous adsorption resin in a vessel. Subsequently, the porous adsorption resin is washed with water, and teicoplanin is eluted from the porous adsorption resin using the eluting agent in which any one or more C1 to C4 water-miscible alcohols is mixed with water in an amount of 40% to 90% (v/v). With respect to this, the porous adsorption resin can include, but is not limited to, DOWEX OPTIPORE L493, DOWEX OPTIPORE L323, DOWEX OPTIPORE SD-2, DIAION HP20, DIAION HP2MG, DIAION HP20SS, SEPABEADS SP825, SEPABEADS SP850, SEPABEADS SP700, SEPABEADS SP207, SEPABEADS SP20SS, AMBERLITE XAD4, AMBERLITE XAD7, AMBERLITE XAD16, and AMBERLITE XAD1600T.

The ultrafiltration process can be applied to separate substances with different molecular weights according to the molecular weight cut-off of a filtration membrane. Batch type or continuous type of ultrafiltration process is carried out according to the structure of the filtration membrane and the filtering device. In the present invention, the term "ultrafiltration" refers to a continuous cross-flow type of ultrafiltration. The liquid contains teicoplanin, purified using the porous adsorption resin and activated carbon, and impurities, mostly macromolecules, such as lipid, protein, and polysaccharide, or colored components combined with the macromolecules or included in the macromolecules. Hence, the impurities have a larger molecular weight than teicoplanin. The reason why the impurities mostly consist of macromolecules is that metabolic products with low molecular weights and components resulting from the culture medium are mostly removed by the porous adsorption resin and activated carbon. The ultrafiltration process is not limited to a process of treating the liquid purified using the porous adsorption resin and activated carbon. In other words, the ultrafiltration process can be carried out as a pre-treatment process before the liquid is treated with the porous adsorption resin. The liquid purified through the ultrafiltration process can be then treated with the porous adsorption resin and activated carbon, and highly pure teicoplanin can be produced. In case that the roughly purified liquid treated with the porous adsorption resin is subjected to the ultrafiltration process without being treated with the activated carbon, the purity of teicoplanin is 90% (w/v) or more.

The ultrafiltration membrane useful in the ultrafiltration process of the present invention can be made of polyether sulfone or regenerated cellulose, and has a molecular weight cut-off of 3,000 Da to 100,000 Da. In certain embodiments, the molecular weight cut-off of the ultrafiltration membrane is 5,000 Da to 50,000 Da. The ultrafiltration membrane can include, but not limited to, Biomax and Ultracel ultrafiltration membrane of Pellicon module, PT and PL ultrafiltration membranes of Prostak module, PT, PL, and Helicon ultrafiltration membrane of Spiral Wound Ultrafiltration module, manufactured by Millipore Co., Sartocon®, and Ultrasart® ultrafiltration membrane, manufactured by Sartorius AG, OMEGA™, ALPHA™, REGEN™, SUPOR® ultrafiltration membranes, manufactured by Pall Co., Filmtec™ ultrafiltration membrane, manufactured by Dow Chemical Co., and Kvick™ ultrafiltration membrane, manufactured by Amersham Pharmacia Biotech Inc.

Water can be added into the liquid following treatment with the porous adsorption resin or treatment with the activated carbon and porous adsorption resin, to reduce the alcohol content in the liquid to 20% (v/v) or less. The ultrafiltration process is then carried out at 8° C. to 30° C., or 12° C. to 18° C., at an input pressure (Pin) of 0 to 4 bar, and a retentate pressure (Pret) of 0 to 3.5 bar. In some embodiments, the input pressure is 0 to 2.5 bar, and the retentate pressure is 0 to 2 bar. In case the liquid is concentrated until a volume of the retentate is $\frac{1}{10}$ or less of the volume of the process liquid before it is subjected to the ultrafiltration process, a diafiltration process can be utilized, in which the purified water is continuously fed into retentate to keep up a constant volume. At this time, a volume of the purified water is 0.5 to 5 times larger than that of the liquid before it is subjected to the ultrafiltration process, and in certain embodiments, the volume of the purified water is 1 to 2 times larger than that of the liquid before it is subjected to the ultrafiltration process.

The liquid being processed, from which polymer impurities and colored components are removed by the ultrafiltration membrane, and which contains teicoplanin, is concentrated using a thin film evaporation system, a reverse osmosis system, or a vacuum distillation system. After acetone is added to the concentrate by a 3 to 10 times larger volume than a concentrate to precipitate teicoplanin for one hour or more, a precipitate is filtered and then dried to produce teicoplanin powder.

The purity of the liquid containing teicoplanin obtained after eluting and/or ultrafiltering a culture broth can be, but is not limited to, at least 60%, less than 90%, 60% to less than 90%, 60%–70%, 70%–80%, or 80% to less than 90%. The purity of teicoplanin obtained after treating the liquid containing teicoplanin with activated carbon and/or ultrafiltering the liquid can be, but is not limited to, 90% or greater, 90%–95%, 90%–96%, 90%–97%, 90%–98%.

Having generally described this invention, a further understanding can be obtained by reference to examples and comparative examples which are provided herein for the purposes of illustration only and are not intended to be limiting unless otherwise specified.

EXAMPLE 1

160 L of culture broth of *Actinoplanes teichomyceticus* DKB 53 was filtered using a drum filter to remove a mycelium therefrom, and 120 L of filtrate was obtained. The filtrate was analyzed by an OPTIMAPAK® C18 (4.6×250 mm, RStech Co.) HPLC column. Teicoplanin 1st International Standard (National Institute for Biological Standards and Control, Hertfordshire UK) was used as a reference standard for quantification. With respect to this, the content and total amount of teicoplanin in the filtrate were 4.2 g/L and 504 g, respectively. Additionally, the pH of the filtrate was 6.8. Four L of methanol was added to 20 L of filtrate (teicoplanin 84 g), and the resulting mixture was applied onto a column (15×50 cm) packed with 4 L of DOWEX OPTIPORE SD-2 at a flow rate of 2 BV (bed volume)/hr without controlling the pH of the resulting mixture. Subsequently, 4 BV (16 L) of 30% (v/v) methanol was loaded at the flow rate of 4 BV/hr into the column to wash the resin packed in the column. Further, 8 BV (32 L) of 60% (v/v) methanol, containing 0.15 M sodium chloride, was loaded into the column at a flow rate of 4 BV/hr to elute teicoplanin. It was confirmed by analysis of an eluate using HPLC that the peak area of teicoplanin A2 was 84.8% of the total peak area, and a roughly purified substance was eluted at relatively high purity. Furthermore, the amount of teicoplanin was 72.2 g, which meant that recovery of teicoplanin was 85.9% (refer to Table 1).

EXAMPLE 2

2 L of isopropanol was added to 20 L of filtered culture broth (teicoplanin 84 g) according to Example 1, and the resulting mixture was applied on a column (15×50 cm) packed with 4 L of DOWEX OPTIPORE SD-2 at a flow rate of 2 BV/hr. Subsequently, 4 BV (16 L) of 15% (v/v) isopropanol was loaded at a flow rate of 4 BV/hr into the column to wash the resin packed in the column. Further, 8 BV (32 L) of 40% (v/v) isopropanol, containing 0.15 M sodium chloride, was loaded into the column at a flow rate of 4 BV/hr to elute teicoplanin. It was confirmed by analysis of an eluate using HPLC that the peak area of teicoplanin A2 was 81.7% of the total peak area. Furthermore, the amount of teicoplanin was 73.6 g, which meant that recovery of teicoplanin was 87.6% (refer to Table 1).

EXAMPLE 3

4 L of methanol was added to 20 L of filtered culture broth according to example 1, and the resulting mixture was applied on a column (15×50 cm) packed with 4 L of Diaion HP 20 at a flow rate of 2 BV/hr. Subsequently, 4 BV (16 L) of 30% (v/v) methanol solution was loaded at a flow rate of 4 BV/hr into the column to wash the resin packed in the column. Further, 8 BV (32 L) of 60% (v/v) methanol solution, containing 0.15 M sodium chloride, was loaded into the column at a flow rate of 4 BV/hr to elute teicoplanin. It was confirmed by analysis of an eluate using HPLC that the peak area of teicoplanin A2 was 83.4% of a total peak area. Furthermore, the amount of teicoplanin was 70.7 g, which meant that recovery of the teicoplanin was 84.2% (refer to Table 1).

COMPARATIVE EXAMPLE 1

After the pH of the filtered culture broth of example 1 was adjusted to 11 using 1N NaOH, 20 L of filtrate was applied on a column (15×50 cm) packed with 4 L of Diaion HP 20 at a flow rate of 2 BV/hr according to a process as disclosed in Korean Pat. No. 321304. Subsequently, 30% (v/v), 50% (v/v), and 80% (v/v) methanol were loaded at a flow rate of 2 BV/hr into the column. At this time, the amount of each methanol solution loaded into the column was 4 BV (16 L). Eluates passed from the column by 50% (v/v) and 80% (v/v) methanol containing teicoplanin were pooled together. With respect to this, it was confirmed by analysis of the mixed eluate using HPLC that a peak area of teicoplanin A2 was 67.4% of a total peak area. Furthermore, the amount of teicoplanin was 53.74 g, which meant that recovery of teicoplanin was relatively low (63.9%, refer to Table 1). Teicoplanin contents in a portion of the solution passing through the column without being adsorbed into Diaion HP 20 when the filtrate with a pH of 11 was applied on the column, and in 30% (v/v) methanol eluate were 11.8% and 21.7% of the teicoplanin content in the filtrated culture broth, respectively. Therefore, it can be seen that a yield of teicoplanin was reduced due to the basic pH of the filtered culture broth during an adsorption process using the porous adsorption resin and a washing process of the porous adsorption resin.

COMPARATIVE EXAMPLE 2

20 L of filtered culture broth according to Example 1 was mixed with 4 L of methanol, and the resulting mixture was applied on a column (15×50 cm) packed with 4 L of Diaion HP 20 at a flow rate of 1.2 BV/hr. Subsequently, 4 BV (16 L) of distilled water was loaded at the flow rate of 2 BV/hr into the column, and 5 BV of 20% (v/v) isopropanol was then loaded into the column to wash the resin packed in the column according to a process as disclosed in Korean Pat. Laid-Open Publication No. 2003-0034949. After the completion of the washing, 4.5 BV of 40% (v/v) isopropanol was loaded into the column to elute teicoplanin from the column. It was confirmed by analysis of the eluate using HPLC that a peak area of teicoplanin A2 was 63.3% of the total peak area. Furthermore, the amount of teicoplanin was 71.2 g, which meant that the recovery of teicoplanin was 84.8% (refer to Table 1). From the comparison of Examples 1, 2, and 3 with comparative Example 2, it can be seen that the roughly purified liquid containing a relatively high content of teicoplanin was yielded from the porous adsorption resin in the case of using the eluent containing a salt.

TABLE 1

Recovery and purity of teicoplanin according to elution conditions when teicoplanin is eluted from the porous adsorption resin

| | Porous adsorption resin | Eluting agent | HPLC peak area of teicoplanin A2 (%) | Recovery (%) |
|---|---|---|---|---|
| Ex. 1 | DOWEX OPTIPORE SD-2 | 60% methanol, 0.15M NaCl | 84.8 | 85.9 |
| Ex. 2 | DOWEX OPTIPORE SD-2 | 40% isopropanol, 0.15M NaCl | 81.7 | 87.6 |
| Ex. 3 | Diaion HP 20 | 60% methanol, 0.15M NaCl | 83.4 | 84.2 |
| Co. Ex. 1 | Diaion HP 20 | 50 to 80% methanol | 67.4 | 63.9 |
| Co. Ex. 2 | Diaion HP 20 | 40% isopropanol | 63.3 | 84.8 |

EXAMPLE 4

A portion of 32 L of roughly purified liquid, containing teicoplanin, that is to say, 8 L of roughly purified liquid (teicoplanin 18 g), according to Example 1 was mixed with 8 L of distilled water in a vessel with a volume of 20 L. The pH of the mixture was adjusted to 7.0 using 0.1 N NaOH. Subsequently, 18 g of Darco KB-B as an activated carbon was added to the mixture, and the resulting mixture was agitated using a mechanical agitator. At this time, the amount of the activated carbon was the same as that of teicoplanin in the roughly purified liquid. Additionally, the resulting mixture was agitated at 28° C. for 2 hours, and then filtered by a KS 80 filter to remove the activated carbon from the resulting mixture. The filtered liquid was applied on a column (15×50 cm) packed with 4 L of DOWEX OPTI-PORE SD-2 at a flow rate of 2 BV/hr. Subsequently, 4 BV (16 L) of distilled water was loaded at the flow rate of 4 BV/hr into the column to wash the resin packed in the column. After the completion of the washing, 2 BV (8 L) of 70% (v/v) methanol was loaded into the column to elute teicoplanin from the column. It was confirmed by analysis of the eluate using HPLC that the purity of teicoplanin was 94.7%, and the amount of teicoplanin was 13.1 g.

20 L of distilled water was added to the eluate to dilute it so that the concentration of methanol was reduced to 20% (v/v) or less. The diluted eluate was filtered by a Biomax 2 ultrafiltration membrane with a molecular weight cut-off of 50,000 Da and a filtering area of 0.1 m$^2$ at Pin of 1 bar and Pret of 0.5 bar. When the volume of the retentate was 2 L or less, the distilled water was fed continuously into the retentate with same flux rate of the ultrafiltration. Thus, the volume of the retentate was maintained at 1.8 to 2 L during the diafiltration process. The total volume of the filtrate, including the diafiltration step, was 42 L. The filtrate was concentrated using a reverse osmosis filtering membrane (Nanomax-50, Millipore Co.) at Pin of 1.5 bar and Pret of 0 bar, and the volume of the concentrate was 500 ml. The concentration was continued while 2 L of distilled water was fed to the concentrate to maintain the volume and 420 ml of concentrate was recovered. With respect to this, it was confirmed by analysis of the concentrate using HPLC that the amount of teicoplanin in the concentrate was 11.8 g. As well, 3.36 L of acetone was slowly added to the concentrate while the concentrate was agitated to precipitate teicoplanin for 12 hours, and the resulting concentrate was filtered by Whatman filter paper 4 to recover a precipitate. The precipitate was dried in a vacuum drier at 40° C. for 6 hours to recover 10.2 g of teicoplanin powder.

The teicoplanin powder was dissolved in distilled water to provide a concentration of teicoplanin of 50 mg/ml. The teicoplanin suspension was compared with Targocid® (Aventis), containing teicoplanin in the same concentration to evaluate the removal of colored components. In detail, the teicoplanin suspension and Targocid® were dispensed in wells of a 96 well plate, and absorbencies were measured at a wavelength of 405 nm using a THERMOmax Microplate reader (Molecular Devices Corp.). In consequence, the teicoplanin powder of the present invention had a lower absorbance than Targocid®. Therefore, it can be seen that teicoplanin with excellent decolorization was produced according to the present invention (refer to Table 2). With reference to FIG. 1, the results regarding the analysis of teicoplanin produced according to Example 4, using an OPTIMAPAK® C18 column are illustrated. At this time, the purity of teicoplanin was 97.8% (w/w).

EXAMPLE 5

A portion of 32 L of roughly purified liquid, containing teicoplanin, that is to say, 8 L of roughly purified liquid (teicoplanin 18.4 g), according to Example 2 was mixed with 8 L of distilled water in a vessel with a volume of 20 L. The pH of the mixture was adjusted to 7.0 using 0.1 N NaOH. Subsequently, 18.4 g of NUCHAR SN-20 as an activated carbon was added to the mixture. At this time, the amount of the activated carbon was the same as that of teicoplanin in the roughly purified liquid. Additionally, the resulting mixture was agitated using a mechanical agitator at 28° C. for 2 hours, and then filtered by a KS 80 filter to remove the activated carbon from the resulting mixture. The filtered liquid was applied on a column (15×50 cm) packed with 4 L of a DOWEX OPTIPORE SD-2 at a flow rate of 2 BV/hr. Subsequently, 4 BV (16 L) of distilled water was loaded at the flow rate of 4 BV/hr into the column to wash the resin packed in the column. After the completion of the washing, 2 BV (8 L) of 40% (v/v) isopropanol was loaded into the column to elute teicoplanin from the column. It was confirmed by analysis of the eluate using HPLC that the purity of teicoplanin was 93.6%, and the amount of teicoplanin was 13.4 g.

24 L of distilled water was added to the eluate to dilute it so that the concentration of isopropanol was reduced to 10% (v/v) or less. The diluted eluate was filtered by a Sartocon ultrafiltration membrane with a molecular weight cut-off of 30,000 Da and a filtering area of 0.1 m² at Pin of 1 bar and Pret of 0.5 bar. When the volume of the retentate was 2 L or less, the distilled water was fed continuously into the retentate with same flux rate of the ultrafiltration. Thus, the volume of the retentate was maintained at 1.8 to 2 L during the diafiltration. The total volume of the permeate, including the distilled water used in the diafiltration, was 48 L. The filtrate was concentrated by a reverse osmosis filtering membrane (Nanomax-50, Millipore Co.) at Pin of 1.5 bar and Pret of 0 bar, and the volume of a concentrate was 480 ml. The concentration was continued while 2 L of distilled water being fed to the concentrate to maintain the volume and 460 ml of concentrate was recovered. It was confirmed by analysis of the concentrate using HPLC that the amount of teicoplanin in the concentrate was 11.9 g. 3.68 L of acetone was slowly added to the concentrate while the concentrate being agitated to precipitate teicoplanin for 12 hours, and the resulting concentrate was filtered by Whatman filter paper 4 to recover a precipitate. The precipitate was dried in a vacuum drier at 40° C. for 6 hours to recover teicoplanin powder. The teicoplanin powder was analyzed using HPLC, and the purity and amount of the teicoplanin powder were 97.1% (v/v) and 10.7 g, respectively. Like in the case of Example 4, the teicoplanin powder was dissolved in distilled water at a concentration of 50 mg/ml, and the absorbance of a teicoplanin suspension was measured at a wavelength of 405 nm (refer to Table 2).

TABLE 2

Absorbance of the teicoplanin suspension

| Sample | Concentration | OD at 405 nm |
|---|---|---|
| Targocid ® | 50 mg/ml | 0.061 |
| Example 4 | 50 mg/ml | 0.031 |
| Example 5 | 50 mg/ml | 0.037 |

EXAMPLE 6

20 L of filtered culture broth according to Example 1 was subjected to an ultrafiltration process before it was adsorbed into a porous adsorption resin. In detail, 20 L of filtered culture broth according to Example 1 was subjected to a ultrafiltration by a Biomax 2 ultrafiltration membrane equipped in ETU-II MF/UF system (Millipore Co.), having a molecular weight cut-off of 50,000 Da and a filtering area of 0.5 m2, at Pin of 2.0 bar and Pret of 1.0 bar without controlling the pH of the culture broth. At this time, when a volume of the retentate was 2 L or less, the distilled water was fed into the retentate with the same flux rate of the ultrafiltration. The total volume of the permeate, including the diafiltration, was 50 L. The permeate was analyzed by HPLC using an OPTIMAPAK® C18 column (4.6×250 mm, RStech Co.). With respect to this, the content and total amount of teicoplanin in the permeate were 1.58 g/L and 79 g, respectively. Hence, recovery yield of teicoplanin was 94%. The permeate was applied on a column (15×50 cm) packed with 4 L of DOWEX OPTIPORE SD-2 at a flow rate of 2 BV (bed volume)/hr. Subsequently, 4 BV (16 L) of 30% (v/v) methanol was loaded at the flow rate of 4 BV/hr into the column to wash the resin packed in the column. Further, 8 BV (32 L) of 60% (v/v) methanol, containing 0.15 M sodium chloride, was loaded into the column at the flow rate of 4 BV/hr to elute teicoplanin. It was confirmed by an analysis of an eluate using HPLC that a peak area of teicoplanin A2 was 87.4% of a total peak area. As well, the amount of teicoplanin was 70 g, which meant that recovery of teicoplanin was 88.6%.

17.5 g of Darco KB-B as an activated carbon was added into a portion of 32 L of eluate passing through the porous adsorption resin, that is to say, 8 L of eluate (containing 17.5 g of teicoplanin), and the resulting mixture was agitated using a mechanical agitator at 28° C. for 2 hours. The agitated mixture was filtered by a KS 80 filter to remove the activated carbon from the mixture. The filtered liquid was applied on a column (5×30 cm) packed with 0.4 L of DOWEX OPTIPORE SD-2 at a flow rate of 4 BV/hr. Subsequently, 4 BV (1.6 L) of distilled water was loaded at the flow rate of 4 BV/hr into the column to wash the resin packed in the column. After the completion of the washing, 2 BV (800 ml) of 70% (v/v) methanol was loaded into the column to elute teicoplanin from the column. 70% (v/v) methanol, which was eluted from the resin and contained teicoplanin, was concentrated by vacuum distillation until its volume was 200 ml. 1.6 L of acetone was slowly added to the concentrate while it being agitated to precipitate teicoplanin for 8 hours, and the resulting mixture was filtered by Whatman filter paper 4 to recover a precipitate. The precipitate was dried in a vacuum drier at 40° C. for 6 hours to recover 10.9 g of teicoplanin powder. The teicoplanin powder was then suspended in distilled water such that a concentration of the teicoplanin was 1 mg/ml. It was confirmed by analysis using HPLC that the purity of teicoplanin was 95.8% (w/w).

EXAMPLE 7

A portion of 32 L of roughly purified liquid, containing teicoplanin and passing through a porous adsorption resin, that is to say, 8 L of roughly purified liquid (teicoplanin 18 g), according to Example 1 was mixed with 16 L of distilled water. A mixture was subjected to ultrafiltration using a Biomax 2 ultrafiltration membrane equipped in ETU-II MF/UF system (Millipore Co.), having a molecular weight cut-off of 50,000 Da and a filtering area of 0.5 m2, at Pin of 2.0 bar and Pret of 1.0 bar. At this time, when the volume of the retentate was 2 L or less, distilled water was fed into the retentate with the same flux rate of the ultrafiltration. A total volume of the permeate, including the diafiltration, was 36 L. The permeate was concentrated by a reverse osmosis membrane (Nanomax-50, Millipore Co.) at Pin of 1.5 bar and Pret of 0 bar, and the volume of a concentrate was 500 ml. Subsequently, the concentration process was continued while 4 L of distilled water being fed to the concentrate with the same flux rate of the reverse osmosis and recovered 380 ml of concentrate. Three L of acetone was slowly added to the concentrate while the concentrate being agitated to precipitate teicoplanin for 12 hours, and the resulting mixture was filtered by Whatman filter paper 4 to recover a precipitate. The precipitate was dried in a vacuum drier at 40° C. for 6 hours to recover 12.9 g of teicoplanin powder. The teicoplanin powder was then dissolved in distilled water to a concentration of 1 mg/ml. It was confirmed by analysis using HPLC that the purity of teicoplanin was 90.2% (w/w).

As described above, the present invention is advantageous in that the production of teicoplanin is carried out within a neutral pH range, thereby ensuring the high stability and improving the purity of teicoplanin. Other advantages are that impurities, such as colored components, are clearly removed, and it is possible to apply the invention to a large scale production of teicoplanin.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention can be practiced otherwise than as specifically described.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A method of producing teicoplanin comprising:
   (a) applying a solution comprising a culture broth containing teicoplanin, from *Actinoplanes teichomyceticus* strain capable of producing teicoplanin, to a porous adsorption resin;
   (b) eluting the teicoplanin from the porous adsorption resin to produce an eluate containing the teicoplanin;
   (c) treating the eluate of (b) containing the teicoplanin with an activated carbon to recover the teicoplanin; and
   (d) ultrafiltering the teicoplanin of (c),
   wherein the eluting in step (b) is performed using an elution agent comprising a neutral salt in a concentration of 0.05M to 0.5M.

2. The method as set forth in claim 1, wherein the *Actinoplanes teichomyceticus* strain is *Actinoplanes teichomyceticus* DKB 53 (KCTC 10587 BP).

3. The method as set forth in claim 1, wherein the eluting of the teicoplanin in step (b) is performed using the elution agent having a pH of 6.0 to 8.0 and further comprising 40% to 90% (v/v) of one or more of C1 to C4 water-miscible alcohols.

4. The method as set forth in claim 1, wherein the eluting of the teicoplanin in step (b) is performed using the elution agent having a pH of 6.0 to 8.0 and further comprising 40% to 90% (v/v) of one or more of C3 to C6 water-miscible ketones.

* * * * *